United States Patent
Cross, III

(10) Patent No.: US 11,304,971 B2
(45) Date of Patent: Apr. 19, 2022

(54) METFORMIN COMPOSITIONS AND METHODS FOR TREATMENT OF DIABETES

(71) Applicant: William H. Cross, III, Waco, GA (US)

(72) Inventor: William H. Cross, III, Waco, GA (US)

(73) Assignee: William H. Cross, III, Waco, GA (US)

( * ) Notice: Subject to any disclaimer, the term of this patent is extended or adjusted under 35 U.S.C. 154(b) by 0 days.

(21) Appl. No.: 16/264,595

(22) Filed: Jan. 31, 2019

(65) Prior Publication Data

US 2019/0231806 A1    Aug. 1, 2019

Related U.S. Application Data

(60) Provisional application No. 62/624,729, filed on Jan. 31, 2018.

(51) Int. Cl.

| | | |
|---|---|---|
| *A61K 31/714* | (2006.01) | |
| *A61K 31/185* | (2006.01) | |
| *A61K 31/4045* | (2006.01) | |
| *A61K 31/155* | (2006.01) | |
| *A61P 3/10* | (2006.01) | |
| *A61K 31/198* | (2006.01) | |

(52) U.S. Cl.
CPC .......... *A61K 31/714* (2013.01); *A61K 31/155* (2013.01); *A61K 31/185* (2013.01); *A61K 31/198* (2013.01); *A61K 31/4045* (2013.01); *A61P 3/10* (2018.01)

(58) Field of Classification Search
CPC ... A61K 31/155; A61K 31/714; A61K 31/185
See application file for complete search history.

(56) References Cited

U.S. PATENT DOCUMENTS

| | | | |
|---|---|---|---|
| 3,711,602 | A | 1/1973 | Herschler |
| 5,719,119 | A | 2/1998 | Veech |
| 7,060,295 | B2 | 6/2006 | Richardson |
| 7,645,742 | B2 | 1/2010 | Stohs |
| 9,414,615 | B2 | 8/2016 | Sridhar |
| 10,945,979 | B1 * | 3/2021 | Schroeder ................. A23L 2/60 |
| 2001/0011083 | A1 | 8/2001 | Barr |
| 2001/0031744 | A1 | 10/2001 | Kosbab |
| 2005/0129783 | A1 | 6/2005 | Mccleary |
| 2011/0313043 | A1 | 12/2011 | Kramer |
| 2012/0232003 | A1 * | 9/2012 | Takahashi ............ A61K 9/0019 514/7.2 |
| 2014/0044685 | A1 | 2/2014 | Greenberg |
| 2016/0228409 | A1 | 8/2016 | Cross |
| 2017/0312329 | A1 | 11/2017 | Cross, III |

FOREIGN PATENT DOCUMENTS

| | | | |
|---|---|---|---|
| CN | 101716182 | * 6/2010 | .......... A61K 31/714 |
| CN | 101716182 | 4/2013 | |
| IN | 1306CHE2007 | 1/2009 | |
| WO | 2008048045 | 4/2008 | |
| WO | 2013108262 | 7/2013 | |

OTHER PUBLICATIONS

McCarty (Healthcare 2017, 5, 15, pp. 1-28).*
Bell, D.S.H., 2012, Case Report in Endocrinology, Article ID 165056, 3pp.
Curtis, L., 2013, International Journal of Diabetes Research, 2:56-60.
Hagen, M. et al., 2017, Current Medical Research and Opinion, 33(9):1623-1634.
Henriksen, E.J., 2006, Free Radical Biology & Medicine, 40:3-12.
Lautt et al., 2010, Can. J. Physiol. Pharmacol., 88:313-323.
Shinohara, T. et al., 2004, J. Biol. Chem., 279:23559-23564.
Vita Sciences, Nervex Neuropathy Pain Relief (Product Literature), Jan. 26, 2017.
Wagner, T., 2012, Pain Management, 2(3):239-250.
Wojtczak, A., 2002, Medical Teacher, 24:658-660.
Yonguc et al., 2015, Gene, 555:119-126.
U.S. Appl. No. 15/017,527, 20160228409, Oct. 11, 2016.
U.S. Appl. No. 15/496,919, 20180303896, Oct. 25, 2018.
U.S. Appl. No. 15/650,825, 20170312329, Sep. 6, 2019.
U.S. Appl. No. 16/264,609, 20190231807, Aug. 1, 2019.
U.S. Appl. No. 16/264,614, 20190231725, Aug. 1, 2019.
U.S. Appl. No. 16/283,660, 20190275154, Sep. 12, 2019.
U.S. Appl. No. 17/325,674.
Mccarty, M.F., 2017, Healthare, 5, 28pp (doi:10.3390/healthcare5010015).

* cited by examiner

*Primary Examiner* — Pancham Bakshi
(74) *Attorney, Agent, or Firm* — Thomas | Horstemeyer LLP

(57) ABSTRACT

The invention provides compositions and methods to treat diabetes with improved formulations in which metformin is combined with at least three antioxidants that contain a stabilizing heteroatom adjacent to a saturated carbon and which help maintain a balance between antioxidant and pro-oxidant properties. The antioxidants include at least the combination of taurine, citrulline and methylcobalamin, and optionally include melatonin. The composition provides management of blood glucose levels comparable to metformin in the same dose without antioxidants, without the phenomenon of undermining metformin performance that is commonly observed in the presence of co-administered antioxidants.

18 Claims, No Drawings

METFORMIN COMPOSITIONS AND METHODS FOR TREATMENT OF DIABETES

CROSS-REFERENCE TO RELATED APPLICATIONS

This application derives priority from provisional application U.S. Ser. No. 62/624,729, filed Jan. 31, 2018 and having the same title and sole inventor.

FIELD OF THE INVENTION

The invention concerns compositions and methods for the treatment and prevention of diabetes.

BACKGROUND

Diabetes mellitus is a carbohydrate metabolism disorder caused by insufficient insulin production and or reduced sensitivity to insulin. Consequently, the cells are inhibited from normal glucose utilization, resulting in abnormally high blood sugar levels and a variety of maladies. Chronic complications include diabetic retinopathy (retinal changes leading to blindness), kidney disease and frequent infection. Acute complications from diabetes may be fatal, such as "dead-in-bed syndrome" and such as "diabetic shock" wherein a diabetic person suddenly and without warning becomes temporarily blind, disoriented and or loses consciousness during normal activity. To date there is no cure for diabetes.

Although complications can often be avoided by careful management of blood glucose levels, complete control has remained elusive. For instance, "hypoglycemia unaware" diabetic persons who comply with medical protocols for insulin administration may nevertheless have hypoglycemic episodes and be completely unaware that diabetic shock is setting in until after the symptoms have manifested. This puts them at risk during sleep, sports, driving, and other daily activities. This also prevents bystanders from calling for timely medical intervention. And the lack of coordination makes the hypoglycemic individual appear to be under the influence of drugs or alcohol. Thus, diabetic drivers in particular are at risk for arrest without culpability, and diabetic drivers of commercial motor vehicles often face bans abroad and onerous compliance requirements under the U.S. federal exemption program.

In addition, diabetes is the main known cause for development of neuropathy in developed countries, affecting almost 2% of the global population and about 20% of the diabetic population, and is the leading cause of morbidity and mortality in diabetes patients. It is believed to be responsible for between 50% and 75% of nontraumatic amputations. Hyperglycemia is the main risk factor. Other factors include the patient's age, smoking, hypertension, height and hyperlipidemia, and length of personal history with diabetes. The symptoms vary with the type of diabetic neuropathy: sensorimotor polyneuropathy first appears as numbness and night-time pain; autonomic neuropathy affects critical organs and may cause cardiac arrhythmias and gastrointestinal symptoms; cranial neuropathies may affect the eye's nerves, movement, focus, and pupil size; mononeuropathies can mimic the symptoms of myocardial infarction and other traumas; entrapment neuropathies often lead to carpal tunnel syndrome. Still other symptoms include weakness, imbalance, muscle contraction, sexual dysfunction, impaired speech, and loss of control over the bowels and or bladder. Several medicinal treatments exist for these various neuropathies, however they have a high incidence of side effects.

Metformin—actually metformin hydrochloride—is the drug of choice to treat diabetes, and is the fourth-most-prescribed drug in the United States with 81 million prescriptions in 2016. It is a biguanide drug, and its physiological mechanism is to lower the liver's production of glucose, and to raise the body's sensitivity to insulin in tissues generally. Metformin's trade names include Glucophage XR®, Carbophage SR®, Riomet®, Fortamet®, Glumetza®, Obimet®, Gluformin®, Dianben®, Diabex®, Diaformin®, Siofor®, Metfogamma®, and Glifor®. In order to boost metformin's efficacy in managing blood sugar levels in type 2 (i.e., adult onset) diabetic patients, the drug has been combined with a variety of other medicines in order to improve its efficacy. These include binary combinations with: thizolidinediones such as rosiglitazone (which has deleterious side effects for the heart) or pioglitazone; dipeptidyl peptidase-4 inhibitors such as sitagliptin, saxagliptin, alogliptin, or linagliptin; sulfonylureas such as glipizide or glibenclamide; and meglitinides such as repaglinide. Metformin has also been formulated in a ternary combination with pioglitazone and glibenclamide.

Despite the drug's widespread use, studies have shown that the potency of metformin is reduced when it is combined with antioxidants, which include not only important drugs but also important nutritional compounds in the diet. Yet raising the dose of metformin can increase lactic acid levels in the blood to a concerning level. Even at ordinary doses Metformin has common side effects, among which are heartburn, stomach pain, nausea or vomiting, gas, diarrhea, constipation, headache, and leaving a metallic taste in the mouth.

Consequently there is an ongoing need for compositions to treat and prevent diabetes.

SUMMARY OF THE INVENTION

The invention provides metformin compositions and methods to treat diabetes and prevent development of diabetes. In particular, the present invention has discovered that combination with certain antioxidants that comprise stabilizing heteroatoms offsets meformin's usual fall in potency when used with antioxidant species.

In certain embodiments the invention provides an improved composition for treatment of diabetes comprising a pharmaceutically effective amount of metformin in combination with a pharmaceutically effective amount of each of a plurality of antioxidant compounds wherein:
  a) the plurality of antioxidant compounds comprises at least three compounds that each contain a stabilizing heteroatom adjacent to a saturated carbon, wherein if the heteroatom is sulfur it is not part of a disulfide bond;
  b) the plurality of antioxidant compounds are present in amounts and ratios that help maintain a homeostatic balance between antioxidant and pro-oxidant properties in the body; and
  c) the antioxidant compounds comprise at least taurine, citrulline and methylcobalamin; and
wherein the composition achieves blood glucose levels within ±5% of those obtained by use of the same dose of metformin over the same period in the absence of added antioxidants.

In various additional embodiments the invention provides a method for treatment of diabetes comprising administering to a diabetic patient a pharmaceutically effective amount of metformin in combination with a pharmaceutically effective amount of each of a plurality of antioxidant compounds wherein:
  a) the plurality of antioxidant compounds comprises at least three compounds that each contain a stabilizing heteroatom adjacent to a saturated carbon, wherein if the heteroatom is sulfur it is not part of a disulfide bond;
  b) the plurality of antioxidant compounds are present in amounts and ratios that help maintain a homeostatic balance between antioxidant and pro-oxidant properties in the body; and
  c) the antioxidant compounds comprise at least taurine, citrulline and methylcobalamin; and
wherein the composition achieves blood glucose levels within ±5% of those obtained by use of the same dose of metformin over the same period in the absence of added antioxidants.

DETAILED DESCRIPTION OF THE INVENTION

The invention may be further understood by consideration of the following definitions for the terms as used herein.

The terms "diabetes" refers to the metabolic disorder and or its symptoms, and has its usual and ordinary meaning in the medicinal arts; the term "diabetic" pertains to patients and medical conditions associated with diabetes. These terms contemplate each of the known types of diabetes including the classically defined categories of gestational diabetes, type 1 diabetes (from birth), and type 2 diabetes (later onset). The terms further includes the five more recently classified genetically distinct groupings of patients, as follows. Cluster 1, currently known as type 1, pertains to severe autoimmune diabetes; it is characterized by insulin deficiency and the presence of autoantibodies; it has been identified in 6-15 percent of subjects. Cluster 2 pertains to severe insulin-deficient diabetes; it is characterized by younger age, insulin deficiency, and poor metabolic control, but no autoantibodies; it has been identified in 9-20 percent of subjects. Cluster 3 pertains to severe insulin-resistant diabetes; it is associated with a significantly higher risk of kidney disease and was identified in 11-17 percent of subjects. Cluster 4 pertains to mild obesity-related diabetes, most common in obese individuals, and has been identified in 18-23 percent of subjects. Cluster 5 pertains to mild age-related diabetes, especially in elderly individuals, and has been identified in 39-47 percent of subjects.

The term "effective to reduce" as used with respect to medicinal treatment of a symptom of diabetes means that the compound is effective to decrease the duration or magnitude of the symptom. The term "effective to mitigate" as used with respect to medicinal treatment of a symptom of diabetes means that the compound is effective to decrease the discomfort or appearance that results from the symptom. The term "effective to reduce or mitigate" as used with respect to medicinal treatment of a symptom of diabetes does not exclude the use of any compound that both reduces and mitigates such a symptom.

The term "composition" as used with respect to a composition for treatment of diabetes means a formulation comprising one or more medicinal substances that are individually or alternatively collectively effective to minimize at least one symptom of diabetes.

The term "pharmaceutically effective amount" as used with respect to an antioxidant, medicinal compound, or salt or ester of one of those, means that the respective substance is pharmaceutically safe and effective at the dose given. Examples of counterions and ester groups that are acceptable for pharmaceutical use are found, for instance, in editions of Remington's Pharmaceutical Sciences. A medicinal compound for which such pharmaceutically effective amounts are particularly applicable in the present invention is metformin.

The phrase "essentially the same" regarding the comparability of blood glucose levels arrived at using metformin alone, with the levels obtained using the invention compositions with the same respective dose of metformin over the same time periods, means that latter value is within a certain percentage of the metformin-alone values, for instance within a range chosen from 1% to 10% difference from the metformin-alone value; a value of ±5% is typical. These values correspond to one or more of those obtained by fasting blood glucose (FBG), post-prandial blood glucose (PPBG), and glycosylated hemoglobin (HbA1c). The HbA1c values are particularly relevant as they reflect trends over longer periods as opposed to short-term rises and falls of blood sugar.

The term "metformin" includes not only the biguanide metformin but also its pharmaceutically acceptable salts and esters. In particular it includes metformin hydrochloride but the invention is not so limited.

The terms "salts" and "esters" have their usual and ordinary meaning in organic chemistry. The term "mixtures" as used with respect to metformin and its derivatives means that more than one such compound is present and that the multiple such compounds are mixed, whether they are metformin and or their salts and or esters.

The terms "antioxidant" and "antioxidant compound" are used interchangeably and refer to compounds that inhibit formation of free radicals by biochemical or other chemical oxidation. The term antioxidant has its usual and ordinary meaning in the chemical and medical arts The term "plurality" as used regarding antioxidant compounds means: more than one such compound is present in the composition; the antioxidant compounds are chemically distinct from one another. As the term is used herein, enantiomers of the same compound are not regarded as chemically distinct, however constitution isomers of the same compound are.

The term "saturated carbon" as used herein refers to a carbon atom that has no multiple bonds.

The term "covalently bonded" has its usual and ordinary meaning in organic chemistry.

The term "stabilizing heteroatom" as used with respect to an atom in an antioxidant molecule means that the atom in view is an atom other than carbon, hydrogen or a metal in an organic molecule, and that the heteroatom is able to stabilize a radical formed on a neighboring saturated carbon such as by donation of electron density into it, or by rearrangement of the unpaired electron within the molecule. In particular embodiments heteroatoms N (nitrogen), S (sulfur), and or O (oxygen) are preferred in the stabilizing moiety—or moieties—in an antioxidant compound. Examples of a neighboring, i.e., adjacent, saturated hydrocarbon include —$CH_2R$, —$CHR^1R^2$, and —$CH_3$, where the R species are atoms or functional groups known in organic chemistry. Preferred examples of antioxidant compounds comprising a stabilizing heteroatom adjacent to a saturated hydrocarbon include taurine, beta-alanine, citrulline, and acetyl-L-carnitine, and in certain particularly preferred embodiments include the use of a mixture of all four.

The term "disulfide bond" means a covalent bond between two sulfur atoms. To say that a sulfur atom is not part of a disulfide bond means that it is not covalently bonded to another sulfur atom.

The term "pro-oxidant" as used herein refers to a compound that has the ability to promote oxidation. Some antioxidant compounds act as pro-oxidants under some conditions. In a preferred embodiment the pro-oxidant activity takes place in liver tissue however the invention is not so limited. A preferred embodiment of an antioxidant compound that has a pro-oxidant effect is taurine. In certain embodiments of the invention taurine is in a mixture with at least one additional antioxidant that has a pro-oxidant effect. The term pro-oxidant as used herein includes but is not limited to compounds for which the ability to be a pro-oxidant is contingent upon conditions, such as whether dioxygen or transition metals are present. Such conditional behavior typically arises where reduction of dioxygen or peroxides is spin-forbidden and thus requires the presence of an intermediate such as a reduced transition metal—which is generated from a higher oxidation state of the metal by the action of the conditional pro-oxidant—in order to reduce the dioxygen or peroxide and have the pro-oxidant effect. The term "conditional pro-oxidant" as used herein refers to such condition-dependent pro-oxidant properties.

The phrase "that help maintain a homeostatic balance between antioxidant and pro-oxidant properties in the body," as used with respect to amounts and ratios of antioxidant compounds relative to one another, means that at least one of the antioxidants in view has a pro-oxidant effect when provided in a pharmaceutically effective amount. The phrase further contemplates that some such antioxidants may be conditional pro-oxidants. As an example, as measured by weight, metformin in the range of 500 to 2,500 parts may be combined with taurine in the range of 50 to 200 parts, citrulline in the range of 25 to 100 parts, and methylcobalamin in the range of 0.040 to 0.440 parts, to obtain a combination that helps maintain a homeostatic balance between antioxidant and pro-oxidant properties in the body. In certain embodiments the homeostatic balance pertains to that in the liver.

The term "cobalamin compound" means cobalamin—also known as Vitamin $B_{12}$—and its derivatives and variants such as salts, esters, and those defined by the bonding arrangement of functional groups at the compound's cobalt atom. Preferred cobalamin compounds have the compound's cobalt atom covalently bonded to -5'-deoxyadenosyl, —$CH_3$, —OH, or —CN; these are respectively adenosylcobalamin, methylcobalamin, hydroxocobalamin, and cyanocobalamin. Methylcobalamin is particularly preferred but the invention is not so limited.

The terms "treatment" and "method of treatment" as used with respect to diabetes contemplates therapeutic treatments as well as preventative treatments.

The terms "administering" and "administration" as used with respect to compounds to treat diabetic neuropathy is not limited by the type of their physical dosing, whether it is oral, buccal, parenteral, transdermal, or some other method of administering a dose.

Turning now to the theory of the invention, metformin's mechanism of efficacy is still only partly understood, though it is clearly multifaceted. However, studies by others have now shown that the potency of metformin is substantially reduced when it is administered in combination with antioxidants. This was a counterintuitive result because metformin itself is a potent antioxidant. As to conditions for its reduced potency, see Wouter De Haes et al., "Metformin promotes lifespan through mitohormesis via the peroxiredoxin PRDX-2," *Proc. Nat. Acad. Sci.*, 111(24):E2501-E2509 (2014) at FIG. 2C and corresponding text regarding the antioxidants N-acetylcysteine (NAC) and butylated hydroxyanisole (BHA). Yet that was not entirely without precedent because it was previously reported that antioxidants inhibit insulin sensitivity that can otherwise be elevated by exercise. See, e.g., M. Ristow, et al., "Antioxidants prevent health-promoting effects of physical exercise in humans," *Proc. Natl. Acad. Sci. USA*, 106(21):8665-8670 (2009) at the abstract.

In fact, contrary to metformin's hypothetical role as an antioxidant itself, De Haes et al. demonstrated that metformin triggers a proliferating cascade of reactive oxygen species (radicals) to create a biochemical signal or switch for improved life expectancy. The response of an antioxidant protein, pyridoxiredoxin, to trigger a separate signaling cascade has been less clear, except that the presence of small-molecule antioxidants at the stage where metformin is involved inhibits its effect. Either way, one can readily perceive that co-administered antioxidants would quench the cascade of radical signals that are initiated by metformin as part of its physiological function.

However, in treating diabetes at least one of the same antioxidants that undermine metformin can outperform it when treatment by either alone is compared, as was reported for N-acetyl-cysteine. See F. Javanmanesh et al., *Gynecol Endocrinol.*, 32(4):285-9 (2016). Thus the nature of the therapeutic incompatibility is not as predictable as one might assume.

Another anomaly has been reported, namely that the antioxidant ascorbic acid (Vitamin C), when co-administered in large amounts (500 mg/day) with metformin, reduced blood sugar levels by amounts ranging from 1.5% (for the HbA1c measure) to ca. 3% (for the post-prandial measure) to 7% (for the fasting measure) relative to metformin in combination with a placebo. The HbA1c comparisons may be the most informative because they reflect trends over longer periods—12 weeks in the case of this study. However, interpretation of the results is not straightforward because the relevant identity of the placebo was neither disclosed nor explained; it is inferred here to be oxalic acid (another antioxidant) which was the matrix used to embed the ascorbic acid. Also, earlier reports by others found Vitamin C had no effect when co-administered in lower amounts. See generally and also at the text concerning reference 16: Ganesh N. Dakhale et al., "Supplementation of Vitamin C reduces blood glucose and improves glycosylated hemoglobin in type 2 diabetes mellitus: A randomized, double-blind study," *Advances in Pharmacological Sciences*, Vol. 2011, Article ID 195271, 5 pages. An additional issue is that ascorbic acid is notoriously unstable when exposed to air, light or heat, especially when liquids are present, thus it is not an ideal antioxidant for the purposes of co-formulation with metformin.

This is, then, an unpredictable art with a variety of unknown mechanisms of action. I have now found that small-molecule antioxidants may accommodate the antidiabetes benefits of metformin so long as one or more antioxidants in the combination also contribute pro-oxidant capabilities. In particular, the antioxidant combination of taurine, citrulline, methylcobalamin, and optionally melatonin provides this effect when each is present in a pharmaceutically effective amount. Two observations rationalize this result or show a potentially illuminating pattern, though this invention is not bound by theory. First, collectively those antioxidants have a pro-oxidizing or conditionally pro-oxidizing effect. Also, each of those antioxidants owes its reducing capacity in part to a stabilizing heteroatom covalently bonded to a saturated carbon atom.

Thus this invention provides metformin compositions and methods to treat and prevent development of diabetes without significant loss of potency though strong antioxidants are present. Without being bound by theory it is also believed that the invention works in part by offsetting biochemical deficiencies caused by metformin; these deficiencies may lead to micro-circulation problems and also absorption problems. Nevertheless the anti-oxidant/prooxidant balance is believed to play the main role and possibly is involved in controlling the physiological pathways responsible for the deficiency effects. Table I further clarifies properties of components of the combinations of the invention.

mg; 80 to 320 mg; 120 to 280 mg; 160 to 240 mg; or about 200 mg. As to citrulline the ranges are: 20 to 180 mg; 40 to 160 mg; 60 to 140 mg; 80 to 120 mg; or about 100 mg. As to methylcobalamin the ranges are: 40 to 440 µg; 80 to 400 µg; 120 to 360 µg; 160 to 320 µg; 200 to 280 µg; or about 240 µg. As to melatonin, the ranges are: 1 to 50 mg; 5 to 45 mg; 10 to 40 mg; 15 to 35 mg; 20 to 30 mg; or about 25 mg.

Optionally additional antioxidants may be included to the extent that they comprise a heteroatom-stabilized saturated carbon and accommodate the desired homeostatic balance

TABLE I

| Compound Description and Use | Structure |
|---|---|
| Metformin in a range of 500 to 2,500 mg; a non-limiting illustrative quantity is 1,500 mg. Metformin is itself normally a powerful anti-oxidant that contains a stabilizing heteroatom. Metformin prevents and relieves oxidative stress and protects the pancreas from oxidative stress-induced damage during diabetic complications. | 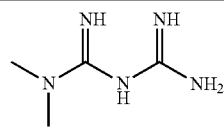<br>Metformin |
| Taurine in a range of 50 to 200 mg; a non-limiting illustrative quantity is 125 mg. Taurine is an antioxidant that comprises a stabilizing heteroatom, relieves oxidative stress, and has a pro-oxidative effect in the liver. | 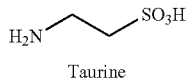<br>Taurine |
| L-Citrulline in a range of 25 to 100 mg; a non-limiting illustrative quantity is 60 mg. Citrulline, an alpha-amino acid, is an antioxidant that comprises a stabilizing heteroatom, relieves oxidative stress in endothelial tissue, and is an essential substrate in enhancing NO-dependent signaling. | 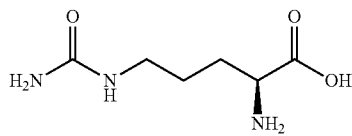<br>Citrulline |
| Methylcobalamin (a form of Vitamin $B_{12}$) in a range of 40 to 440 µg; a non-limiting illustrative quantity is 240 µg. Methylcobalamin is an antioxidant that comprises a stabilizing heteroatom and among other properties can bind the oxidant nitric oxide (NO). | 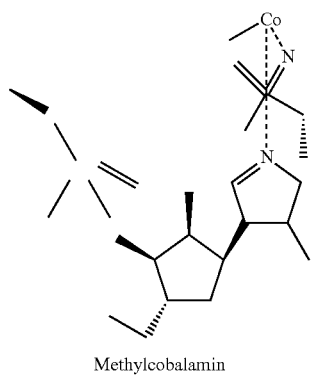<br>Methylcobalamin |
| Melatonin in a range of 1 to 50 mg; a non-limiting illustrative quantity is 25 mg. Melatonin is a weak antioxidant containing a stabilizing heteroatom. It is a highly efficient direct free-radical scavenger; also stimulates antioxidant enzymes; reduces the activation of pro-oxidant enzymes; yet maintains homeostasis in the mitochondria, where 90% of the body's oxidation activity occurs. Melatonin is a conditional pro-oxidant. | 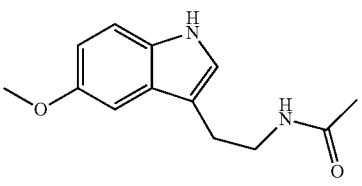<br>Melatonin |

For treatment of diabetes, the present invention has found it useful to provide an ordinary dose of metformin within the composition, i.e., in the following ranges: 500 to 2,500 mg; 750 to 2,250 mg; 1,000 to 2,000 mg; 1,250 to 1,750 mg; or about 1,500 mg.

In certain preferred embodiments the composition provides additional antioxidants in the following non-limiting illustrative ranges. As to taurine the ranges are: 40 to 360 between antioxidant between pro-oxidant species. For instance, acetyl-L-carnitine is an antioxidant that is also a pro-oxidant in the liver. And beta-alanine is an antioxidant that does not interfere with the antioxidant/pro-oxidant balance in the tissues where it is present. In certain preferred embodiments the composition provides acetyl-L-carnitine in the ranges of: 40 to 360 mg; 80 to 320 mg; 120 to 280 mg; 160 to 240 mg; or about 200 mg. In some preferred embodiments the composition provides beta-alanine in the ranges of: 10 to 90 mg; 20 to 80 mg; 30 to 70 mg; 40 to 60 mg; or about 50 mg.

In certain embodiments compositions of the invention comprise one or more adjuvants. Non-limiting illustrative examples of such adjuvants include: analgesic adjuvants; inorganic compounds such as aluminum and or phosphate compounds; a mineral oil such as paraffin oil; dead bacteria such as *Bordetella pertussis, Mycobacterium bovis*, and toxoids; organic compounds such as squalene; delivery systems such as detergents; plant saponins; cytokines; combinations such as Freund's complete or Freund's incomplete adjuvant; and food-based oils such as Adjuvant 65, which is based on peanut oil. The terms in this paragraph are used with their usual and ordinary meaning in the art of formulation for drugs and dietary supplements.

In various embodiments compositions of the invention comprise one or more excipients. Non-limiting illustrative examples of such excipients include: antiadherents, binders, coatings, colors; disintegrants; flavors; glidants; lubricants; preservatives; sorbents; sweeteners; and vehicles. The terms in this paragraph are used with their usual and ordinary meaning in the art of drug formulation.

Normally metformin's effects begin to appear within 48 hours after the user starts taking the medication, and this is considered to be quick-acting. The maximum effect can be seen within four to five days, depending on the dose. However, typically, new users begin at 500 mg/day and over a period of a few weeks increase use to 1,500 or more mg/day. This gradual break-in period is intended to avoid the appearance of side effects, but it slows the arrival of maximum benefits for new users because 1,500 mg/day is the low threshold at which the drug's effects on blood glucose levels become significant.

The measure of efficacy for the invention is that it achieves essentially the same blood glucose levels over the same periods as when the user receives same dose of metformin in the absence of added antioxidants. By essentially the same is meant that the blood glucose levels obtained with the composition are within a range that is within a certain percentage of the levels obtained by use of metformin over the same period in the absence of added antioxidants. In particular embodiments the levels obtained with the invention are within the following percentages of values obtained with the same dose of metformin in the absence of added antioxidants: ±10%; ±9%; ±8%; ±7%; ±6%; ±5%; ±4%; ±3%; ±2%; or ±1%. A value of ±5% is typical. The benefit is that users do not need to sacrifice the full health benefits of metformin in order to include a normal level of several antioxidants in their dietary and or medicinal regimes. Suitable measures for making the comparisons include fasting blood glucose (FBG); post-prandial blood glucose (PPBG); glycosylated hemoglobin (HbA1c). The HbA1c value is particularly preferred because it reflects average trends over time as opposed to point values, however the invention is not so limited.

Consideration of Table II and the examples below may further clarify the scope of the invention, where metformin is provided in the form of its free base or as the hydrochloride salt.

TABLE II

| EXAMPLE | METFORMIN AMOUNT | ANTIOXIDANTS AND AMOUNTS |
| --- | --- | --- |
| 1 | 1,500 mg | 200 mg taurine |
|   |   | 100 mg citrulline |
|   |   | 240 µg methylcobalamin |
| 2 | 1,500 mg | 200 mg taurine |
|   |   | 100 mg citrulline |

TABLE II-continued

| EXAMPLE | METFORMIN AMOUNT | ANTIOXIDANTS AND AMOUNTS |
| --- | --- | --- |
|   |   | 240 µg methylcobalamin |
|   |   | 25 mg melatonin |
| 3 | 500 mg | 40 mg taurine |
|   |   | 20 mg citrulline |
|   |   | 40 µg methylcobalamin |
| 4 | 500 mg | 40 mg taurine |
|   |   | 20 mg citrulline |
|   |   | 40 µg methylcobalamin |
|   |   | 10 mg melatonin |
| 5 | 1,000 mg | 40 mg taurine |
|   |   | 20 mg citrulline |
|   |   | 40 µg methylcobalamin |
| 6 | 2,500 mg | 360 mg taurine |
|   |   | 180 mg citrulline |
|   |   | 440 µg methylcobalamin |
|   |   | 50 mg melatonin |
| 7 | 750 mg | 80 mg taurine |
|   |   | 140 mg citrulline |
|   |   | 120 µg methylcobalamin |
|   |   | 200 mg acetyl-L-carnitine |
|   |   | 50 mg beta-alanine |
| 8 | 2,000 mg | 300 mg taurine |
|   |   | 75 mg citrulline |
|   |   | 320 µg methylcobalamin |
|   |   | 20 mg melatonin |
|   |   | 300 mg acetyl-L-carnitine |
| 9 | 1,200 mg | 120 mg taurine |
|   |   | 90 mg citrulline |
|   |   | 260 µg methylcobalamin |
|   |   | 70 mg melatonin |
|   |   | 90 mg beta-alanine |
| 10 | 1,500 mg | 200 mg taurine |
|   |   | 100 mg citrulline |
|   |   | 240 µg methylcobalamin |
|   |   | 25 mg melatonin |
|   |   | 200 mg acetyl-L-carnintine |
|   |   | 50 mg beta-alanine |

Example 11

A solid dose of 1,500 mg metformin hydrochloride was coadministered with 200 mg taurine, 100 mg citrulline, and 240 µg methylcobalamin. The patient was a middle-aged type 2 diabetic male. For the first five days the patient was dosed in this way every 2 to 4 hours as needed, for a total of 4 to 6 doses per day, and thereafter took a dose every 2 to 6 hours as needed, for a total of 2 to 6 capsules per day. As measured by blood sampling and test strips the combination moved blood glucose levels to essentially the same degree over comparable time horizons, within a range of about ±5% relative to results obtained over the course of a month by administration of metformin hydrochloride alone. Relative to taking metformin hydrochloride alone, the patient also reported that the invention composition provided a notable improvement in circulation within 5 days of beginning to take the invention composition, as manifested by warmer feet and more comfort during the day. He also reported that with use of the invention composition his sleep every night was much improved relative to taking metformin hydrochloride alone.

Example 12

The same dosing protocol as in Example 11 was used for an elderly type 2 diabetic female patient. She reported essentially the same results, and also noted that relative to use of metformin alone, the invention composition improved circulation in her feet within 3 to 5 days of beginning its use, and that it improved her lower limb function.

The embodiments of the invention as described herein are merely illustrative and are not exclusive. Numerous additions, variations, derivations, permutations, equivalents, combinations and modifications of the above-described invention will be apparent to persons of ordinary skill in the relevant arts and are within the scope and spirit of the invention. The invention as described herein contemplates the use of those alternative embodiments without limitation.

The invention claimed is:

1. A composition for treatment of diabetes comprising a pharmaceutically effective amount of metformin and
   (a) taurine in an amount from 50 mg to 200 mg;
   (b) citrulline in an amount from 25 mg to 100 mg;
   (c) methylcobalamin in an amount from 40 µg to 440 µg; and
   (d) beta-alanine in an amount from 10 mg to 90 mg.

2. The composition of claim 1, wherein the composition further comprises melatonin.

3. The composition of claim 1 wherein the composition comprises metformin in an amount from 500 mg to 2,500 mg.

4. The composition of claim 1 wherein the composition comprises metformin in an amount from 500 mg to 2,500 mg;
   melatonin in an amount from 1 to 50 mg.

5. The composition of claim 1 wherein the composition comprises:
   a) metformin in an amount of 1,500 mg;
   b) taurine in an amount of 125 mg;
   c) citrulline in an amount of 60 mg; and
   d) methylcobalamin in an amount of 240 µg.

6. The composition of claim 1 wherein the composition comprises:
   a) metformin in an amount of 1,500 mg;
   b) taurine in an amount of 125 mg;
   c) citrulline in an amount of 60 mg;
   d) methylcobalamin in an amount of 240 µg; and
   e) melatonin in an amount of 25 mg.

7. The composition of claim 1 wherein the amount of taurine is selected from a range that is from 8% to 12% of the amount of metformin by weight.

8. The composition of claim 1 wherein the amount of citrulline is selected from a range that is from 3% to 7% of the amount of metformin by weight.

9. The composition of claim 1 wherein the amount of taurine is selected from a range that is from 150% to 250% of the amount of citrulline by weight.

10. A method for treatment of diabetes comprising administering to a diabetic patient having the composition of claim 1.

11. The method of claim 10, wherein the composition further comprises melatonin.

12. The method of claim 10 wherein the composition comprises metformin in an amount from 500 to 2,500 mg.

13. The method of claim 10 wherein the composition comprises metformin in an amount selected from the range of 500 to 2,500 mg;
    melatonin in an amount from 1 mg to 50 mg.

14. The method of claim 10 wherein the composition comprises:
    a) metformin in an amount of 1,500 mg;
    b) taurine in an amount of 125 mg;
    c) citrulline in an amount of 60 mg; and
    d) methylcobalamin in an amount of 240 µg.

15. The method of claim 10 wherein the composition comprises:
    a) metformin in an amount of 1,500 mg;
    b) taurine in an amount of 125 mg;
    c) citrulline in an amount of 60 mg;
    d) methylcobalamin in an amount of 240 µg; and
    e) melatonin in an amount of 25 mg.

16. The method of claim 10 wherein the amount of taurine is selected from a range that is from 8% to 12% of the amount of metformin by weight.

17. The method of claim 10 wherein the amount of citrulline is selected from a range that is from 3% to 7% of the amount of metformin by weight.

18. The method of claim 10 wherein the amount of taurine is selected from a range that is from 150% to 250% of the amount of citrulline by weight.

* * * * *

UNITED STATES PATENT AND TRADEMARK OFFICE
CERTIFICATE OF CORRECTION

PATENT NO. : 11,304,971 B2  Page 1 of 1
APPLICATION NO. : 16/264595
DATED : April 19, 2022
INVENTOR(S) : William H. Cross, III It is certified that error appears in the above-identified patent and that said Letters Patent is hereby corrected as shown below:

In the Specification

Column 7, Lines 35-50:
The structure of Methylcobalamin should be shown as:

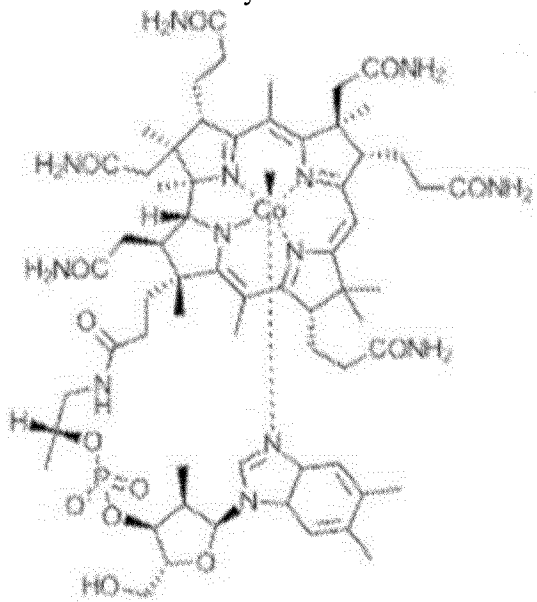

-- --.

Signed and Sealed this
Seventeenth Day of October, 2023

Katherine Kelly Vidal
*Director of the United States Patent and Trademark Office*